United States Patent
de Vries

(10) Patent No.: US 8,329,204 B2
(45) Date of Patent: Dec. 11, 2012

(54) METHOD OF TREATING BONE WITH A CURABLE COMPOSITION

(75) Inventor: Alexander Cornelis de Vries, Rotterdam (NL)

(73) Assignee: Alexander Cornelis de Vries, Rotterdam (NL)

( * ) Notice: Subject to any disclaimer, the term of this patent is extended or adjusted under 35 U.S.C. 154(b) by 304 days.

(21) Appl. No.: 12/710,635

(22) Filed: Feb. 23, 2010

(65) Prior Publication Data

US 2010/0211072 A1  Aug. 19, 2010

Related U.S. Application Data

(62) Division of application No. 10/751,002, filed on Jan. 2, 2004, now Pat. No. 7,670,622.

(30) Foreign Application Priority Data

Jan. 2, 2003 (EP) ..................................... 03075001

(51) Int. Cl.
*A61F 2/02* (2006.01)
(52) U.S. Cl. ....................................................... 424/425
(58) Field of Classification Search .................. None
See application file for complete search history.

(56) References Cited

U.S. PATENT DOCUMENTS

| 4,429,062 A | 1/1984 | Pásztor et al. |
| 6,306,177 B1 | 10/2001 | Felt et al. |

FOREIGN PATENT DOCUMENTS

| EP | 0 667 131 A2 | 8/1995 |
| EP | 0 667 131 B1 | 8/1995 |
| NL | 1005190 | 8/1998 |
| WO | 95/08289 | 3/1995 |
| WO | 96/18427 | 6/1996 |
| WO | WO 01/49327 | * 7/2001 |

OTHER PUBLICATIONS

English abstract of EP 0 667 131, Aug. 1995.
English abstract of NL 1 005 190, Aug. 1998.

* cited by examiner

*Primary Examiner* — Carlos Azpuru
(74) *Attorney, Agent, or Firm* — Banner & Witcoff, Ltd.

(57) ABSTRACT

The present invention relates to a biocompatible polymer composition suitable for bone repair and a method of treating bone repair using a curable polymer composition wherein the cured composition has an elongation until rupture of at least 10%.

15 Claims, 4 Drawing Sheets

METHOD OF TREATING BONE WITH A CURABLE COMPOSITION

RELATED APPLICATIONS

This application is a divisional of U.S. application Ser. No. 10/751,002 filed Jan. 2, 2004 now U.S. Pat. No. 7,670,622 which claims the benefit of EP patent application number 03075001.2 filed Jan. 2, 2003, both of which are hereby incorporated herein by reference in their entireties.

FIELD OF THE INVENTION

The invention relates to a biocompatible polymer composition, suitable for in vivo vessel repair, e.g. for repairing an aortic aneurysm.

BACKGROUND

Aneurysms are local dilatations in blood vessels, in particular arteries that gradually enlarge in time. Unless an aneurysm is adequately treated, it may eventually rupture and cause severe damage to the body, possibly even result in shock or death. Aortic aneurysms are in particular an important cause of death in human adults of 55 years and older.

Traditional repair of an aneurysm entails a major operation with an incision into the aneurysm, evacuation of the clot that is usually contained within, placement of a synthetic graft and wrapping of the graft with the remnants of the artery wall.

A more recent development is the endovascular stent technique. This procedure does not require general anaesthesia and can be done less invasively by simply placing a self-expanding stent via a catheter passed through one of the femoral arteries into the aneurysm to stabilise it. Less fit patients are able to withstand the procedure, hospital stay is cut to 1 to 2 days, and post-operative recovery is shortened considerably.

In WO 95/08289 it is proposed to repair cardiovascular anomalies via the introduction of a photo-activatable biopolymer, which is introduced to the anomaly via a catheter system, after which the polymer is cross-linked. The publication mentions several examples of potentially suitable polymers, wherein it is suggested to be advantageous that the polymers are not only photo-activatable but also biodegradable and resorbable.

A catheter system for delivering fluid materials, such as medicaments to a body vessel is reported in EP 0 667 131 A2. The fluid material is for example a mixture comprising an epoxy resin that cures in the presence of ions.

WO 96/182427 relates to an in situ stent forming catheter for delivering drugs and other fluid materials to an isolated area of a human vessel. As examples of fluid materials, mixtures comprising moisture curing polymeric materials are mentioned, such as cyanoacrylate, polymethylacrylate, polylactic acid and polyglycolic acid.

The American U.S. Pat. No. 6,306,177 describes a method and a related composition for repairing tissue, in particular bone and cartilage. The method involves the use of a curable polyurethane. The publication describes curable polyurethane compositions in general terms and is silent about specific characteristics of a composition for use in (aortic) aneurism repair, such as the viscosity requirements in combination with specific required or desired physical features of the cured compositions, inside the blood vessel.

The Dutch patent 1 005 190 discloses an apparatus for treating a body cavity or body vessel with a curable material, such as polyurethane (PUR). It is described that the apparatus can be used in the treatment of an aorta aneurysm.

Although considerable attention has been paid to the development of delivery systems for fluid material to a body cavity or vessel, it has been found that the availability of compositions for treating cavities or vessels in vivo, in particular for repairing an aneurysm, is highly unsatisfactory.

In particular, it has been found that known polymer compositions suffer from one or more drawbacks, e.g. known compositions have been found to show unsatisfactory handling characteristics, unfavourable curing behaviour, a relatively high level of toxicity, too low biocompatibility, too high thrombogenicity and/or insufficient durability in vivo.

SUMMARY

Accordingly, it is an object of the present invention to provide a novel polymer composition that can be used for treatment of cavity or vessel, in particular for the repair of an aneurysm that can be used as an alternative to known compositions.

It has been found that this object is achieved by a specific fluid biocompatible polymer composition having a viscosity in a specific range. Accordingly, the present invention relates to a fluid biocompatible polymer composition, suitable for vessel repair—in particular for aneurysm repair—said composition comprising a matrix pre-polymer, a filler and a curing agent, wherein said composition has a viscosity at 25° C., as measured by a Brookfield viscosimeter, UK, of 2 000-12 000 cSt (corresponding to 2-12 Pa·s for a composition with a density of 1 000 kg/m$^3$), which polymer is curable in an aqueous environment at a temperature of 37° C. It has been found that such a polymer on the one hand, has a satisfactory flowability to allow a sufficiently swift administration to an aneurysm and on the other hand, allows sufficiently fast curing into a fixed structure to avoid too long disconnection of the blood recirculation during an aneurysm repair.

Moreover, it has been found that satisfactory curing is achieved without excessive heat release.

Such a composition has been found to have particularly favourable handling characteristics. The composition has a suitable flowability to allow introduction of the composition at a site to be repaired in situ through a narrow catheter (e.g. with an inner diameter of approximately 1-1.2 mm and a length of about 50-60 cm length) in a sufficiently short time, typically within 1-2 min. Further, it has been found that during application, the composition does not leak out of the application system used to introduce the composition in situ (e.g. at a connection between pump and catheter) if a contrast medium is used for introducing and position the catheter in place. As a contrast medium e.g. a water based X-rays contrast fluid, such as Omnipaque® (e.g. at a concentration of 300 mg iodine/ml), may be used.

It has further been found that this object is achieved by a fluid biocompatible polymer composition having particular mechanical properties. Accordingly, the present invention relates to a fluid biocompatible polymer composition, suitable for aneurysm repair, comprising a matrix pre-polymer, a filler and a curing agent which biocompatible polymer composition is curable in the presence of a curing catalyst at 25° C. to form a cured material with an elongation until rupture of at least 5% and/or an elastic modulus of at least 1 MPa. It has been found that such a composition is capable of repairing an aneurysm and also contributes positively to the prevention of further dilatation of the vessel at the site of the repaired aneurysm.

BRIEF DESCRIPTION OF THE DRAWINGS

The foregoing and other features and advantages of the present invention will be more fully understood from the following detailed description of illustrative embodiments taken in conjunction with the accompanying drawings in which.

DETAILED DESCRIPTION

Figure 1:
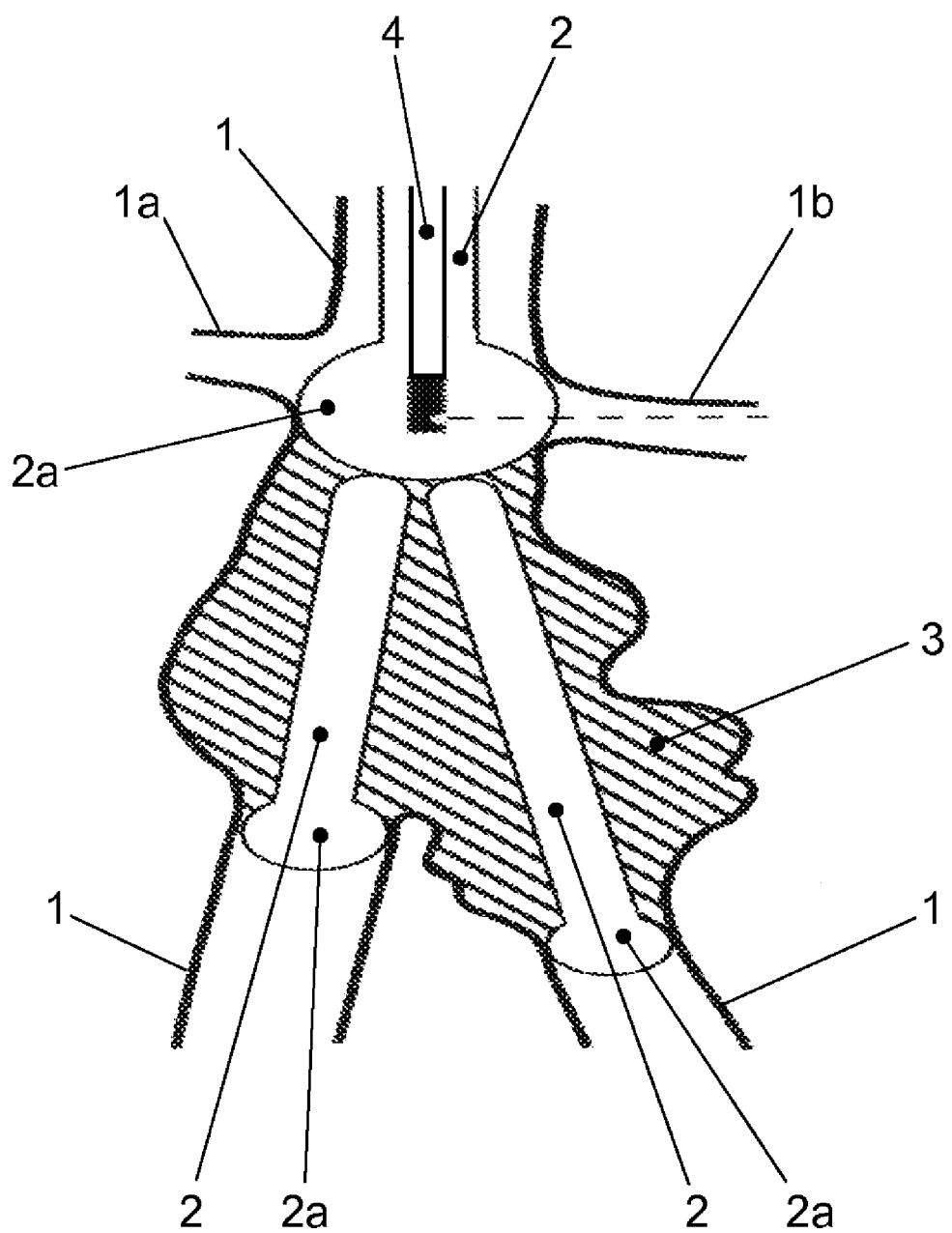
FIG. 1 schematically depicts an aneurysm in the aorta.

In particular, the present invention relates to a biocompatible polymer composition, suitable for treating a blood vessel, in particular for aneurysm repair, comprising a matrix pre-polymer, a filler and a curing agent, wherein said composition has a viscosity at 25° C., as measured by Brookfield viscosimeter of 2 000 to 12 000 cSt, which biocompatible polymer composition is curable in the presence of a curing catalyst at 37° C. to form a cured material with an elongation until rupture of at least 5% and an elastic modulus of at least 1 MPa.

It has been found that a composition according to the invention shows very favourable handling properties before application to a body vessel or cavity. It allows mixing with optionally added other ingredients, e.g. as indicated below, adequate application in a fluid state to the site that is to be repaired (such as an aneurysm) in an acceptable time-frame to avoid inclusion of anomalies—such as air bubbles—in the composition. Accordingly, a composition according to the invention is preferably essentially free of a gas phase.

It has been found that upon curing of a composition according to the invention, the resulting material has a very good durability in that it is capable of maintaining satisfactory mechanical properties and its integrity for a prolonged time, even up to or exceeding a patient's lifetime.

It has been found that a composition according to the invention is capable of curing in vivo into a material having a sufficiently high strength to function as an arterial graft.

A composition according to the invention that has been cured has been found to have a highly satisfactory resistance to abrasion when implemented in an artery.

The viscosity as defined herein is the kinematic viscosity in cSt as measured by Brookfield viscosimeter (UK), model ND J-1 and/or rheometer RMS 800 from Rheometrics, USA. The kinematic viscosity of a fluid in cSt corresponds to the dynamic viscosity in mPa·s divided by the density of the fluid in $g/cm^3$.

The elongation until rupture is defined herein is the value as measured by a Zwick 1445 tensile strength tester (Germany).

The elastic modulus as defined herein is the value as measured by dynamic mechanical analyser, DMA 7 from Perkin-Elmer (USA).

Preferably, the viscosity of the biocompatible polymer composition is in the range of 3 000 to 10 000 cSt, more preferably 4 000 to 8 000 cSt. Particularly good results have been achieved with a composition having a viscosity of approximately 5 000 to 7 000 cSt. Such a polymer composition is found to have particular satisfactory mechanical properties (after curing), in combination with sufficient flowability (before curing).

After curing, the elongation until rupture of the cured composition is preferably at least 10%, more preferably at least 25% even more preferably at least 50%. The upper limit is in practice not particularly important. Very good results have for example been reached with a cured composition having an elongation until rupture of 500% or less, more in particular of 250% or less.

The elastic modulus is preferably at least 2 MPa, more preferably at least 3 MPa, even more preferably at least 4 MPa.

The upper limit is not particularly critical. Very good results have been achieved with a composition having an elastic modulus of less than 20 MPa, after curing.

It has been found that a composition giving rise to a elastic modulus of about 5-15 MPa, is particularly advantageous with respect to the durability of the cured material under in vivo aortic conditions.

Preferably, after curing of the composition the resulting material has a stress value of at least 5 kPa at 1% strain, more preferably of at least 30 kPa at 20% strain, even more preferably a stress value of at least 1 MPa at 50% strain (As determined with Zwick 1445 or with DMA 7, Perkin-Elmer).

The glass transition temperature (Tg) of a cured material obtained from a composition according to the invention is typically less than 37° C. Preferably the Tg is less than 25° C. Very good results have been achieved with a material having a Tg of less than −25° C. (Tg is the value as measured by differential scanning calorimetry (DSC) on a DSC 7, Perkin-Elmer.

The composition is preferably chosen such that the absolute value of the curing enthalpy of the biocompatible polymer composition is less than 10 J/g, as measured by determining the heat production during curing by DSC (DSC 7, Perkin-Elmer).

The components of a composition according to the invention can be prepared by mixing the component in a common mixing device. Particularly suitable is a high shear mixer or an ultrasonic mixer. Suitable mixing conditions can be routinely determined by the skilled person based upon common general knowledge and the information disclosed herein. Very suitable is for example an intermittent mixing procedure (e.g. at 20 000 to 30 000 rpm for a 100 ml composition), wherein between periods of mixing (e.g. of 1-20 min) the composition is allowed to rest in order to cool down (e.g. for 1 to 10 min).

The components or the composition itself should preferably be sterile or sterilisable. At least when present in the composition, the components should have a sufficient hemocompatibility, when used in a blood vessel and are preferably non-thrombogenic and non-tumorogenic.

The term matrix pre-polymer is used herein to describe a curable monomer, a curable oligomer or a curable polymer. Before curing the matrix pre-polymer typically comprises one or more functional groups that allow further polymerisation, e.g. by cross-linking, to form the matrix of the composition after it has been cured. It is stressed that the terms pre-polymer and polymer are to be interpreted broadly, with respect to the number of monomeric units.

The number of monomeric units or molecular weight of the matrix pre-polymer is not particularly critical, as long as it provides a suitable viscosity in the composition. Good results have been obtained with a matrix pre-polymer having at least 1, preferably at least 5, more preferably at least 20 monomeric units, before curing is initiated. For practical reasons, the matrix-polymer generally comprises less than 20 000 monomeric units, preferably less than 1 000, more preferably less than 100, before curing is initiated.

Very good results have been achieved with a composition comprising a matrix pre-polymer having 1 to 5 monomeric units.

The number average molecular weight of the matrix pre-polymer may for example be in the range of 500 to 400 000 gram/mol, preferably in the range of 6 000 to 280 000 gram/mol. As a matrix pre-polymer, any biocompatible pre-polymer can be used that is curable under physiological conditions into a material with satisfactory mechanical properties and that can be delivered to the site inside the body where it is to cure.

The amount of matrix prepolymer can be chosen within wide limits, depending upon the desired viscosity and other properties and may be adequately determined by the skilled professional. Preferably the concentration of the matrix pre-polymer is 10 to 85 wt. % based on the total weight of the composition, more preferably the concentration is in the range of 50 to 75 wt. %. Very good results have been achieved with a composition having an amount of matrix pre-polymer in the range of 60 to 70 wt. %. Examples of suitable matrix pre-polymers are silicon (pre-)polymers, polyurethanes, and combinations thereof such as blends, hybrid polymers and copolymers comprising silicon (pre-)polymers and/or polyurethanes.

Particular suitable hybrid polymers are polymers filled with a molecular silica. A particular preferred molecular silica in a hybrid polymer is a polyhedral oligomeric silsesquioxane (P.O.S.S.). Such a molecular silica is commercially available from Hybrid Plastics, USA under the trademark POSS™.

Preferably the pre-polymer reacts essentially without forming a rest-product, such as a gas (e.g. $CO_2$) or another residual product. Such rest products may be detrimental to the properties, in particular physical properties, of the cured composition.

A preferred matrix pre-polymer is a silicon (pre-)polymer, which is an example of a pre-polymer that usually reacts without forming a rest product. It has been found that a composition comprising a silicon (pre-)polymer is not only very suitable for repairing an aneurysm in such a way that the repaired blood vessel has very satisfactory mechanical properties for a prolonged period of time, but that such a (pre-) polymer in a composition according to the invention also offers the advantages of being hemocompatible, non-thrombogenic, highly biocompatible and non-carcinogenic.

Further it has been found that a composition comprising a silicon (pre-)polymer is capable of curing fast, typically within 5 min. or less—preferably within 2-3 min or less—without generating excessive heat that may do damage to the body or may give rise to defects in the cured material. Further a composition comprising a silicon (pre-)polymer has been found to be particularly suitable to prevent further dilatation of a vessel, e.g. of an aorta at the site of a repaired aneurysm.

It has been found that a composition comprising a silicon (pre-) polymer is very suitable to repair an aneurism. The durability of the cured material has been found to be very high. Life-times of 10-40 years or more are considered to be feasible (based upon stretch test in an in vitro simulation, simulating heart function at 60 beats per minute).

Preferably a silicon (pre-)polymer used in a composition according to the invention has a start viscosity (i.e. before mixing it to a composition according to the invention) of at least 300 cSt. More preferably the start viscosity is in the range of 300 to 1 500 cSt.

Highly preferred is a polydialkylsiloxane polymer, comprising at least two vinyl groups, preferably at the terminal ends. Very good results have been achieved with a polydialkylsiloxane polymer having 3-5 vinyl groups.

Very good results have been achieved with a polydimethylsiloxane monopolymer or a polydialkylsiloxane copolymer—e.g. a block copolymer, a random copolymer or an alternating copolymer—mainly comprising dimethylsiloxane units. A highly preferred polydimethylsiloxane polymer is shown in formula 1 formula 1

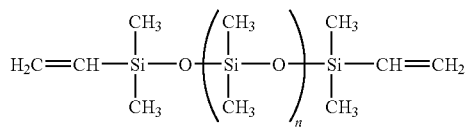

Preferably the number average weight in case this polymer is used is chosen in the range of 20 000 to 200 000 g/mol.

A silicon (pre-)polymer is in practice preferred over polyurethanes, in particular when used for aneurism repair. It has been found that in a composition wherein the matrix pre-polymer is a polyurethane pre-polymer, the heat generation tends to be quite large. Further the $CO_2$ formed during the polymerisation may adversely affect physical properties such as the elongation up to rupture, the elastic modulus and the durability.

Curing can be achieved in many ways, e.g. by the presence of a curing agent and/or by irradiation, in particular irradiation with UV light. The use of UV-light may for example be suitable in case of a local repair. In practice, generally no exposure to radiation is required.

Preferably curing occurs by the presence of a curing agent. The use of a curing agent is particularly preferred. A curing agent as defined herein is any agent that can react with the matrix pre-polymer to result in a solidification (e.g. by cross-linking or gelling) of the composition. Curing agents include cross-linking agents and agents that cure the composition in any other way. Preferably the curing agent is a cross-linking agent. The curing agents can be chosen from the group of curing agents that are suitable to react with the chosen matrix pre-polymer.

A suitable amount of curing agent can easily be determined, depending upon the type of curing agent and the quantity and nature of the other components in the composition. Preferably, the curing agent is present in an amount of at least 0.1 wt. % based on the total weight of the composition, more preferably at least 5 wt. %. The amount of curing agent is preferably less than 15 wt. %, more preferably less than 10 wt. %.

Preferably the curing agent is present in the composition in an amount providing a number of functional groups in the range of 1-10 times the number of functional groups that is provided by the matrix pre-polymer.

Functional groups, as used herein, are those functional groups that are capable of participating in the curing, in particular by being capable of reacting with a functional group of another molecule (curing agent or matrix pre-polymer) in the composition. Examples of functional groups are vinyl groups, acryloyl groups, methacryloyl groups and hydride groups. Vinyl groups are in particular preferred in the matrix pre-polymer. Hydride groups are in particular preferred in the curing agent.

Examples of suitable curing agents are polyalkylhydrosiloxane polymers, including fluorinated polyalkylhydrosiloxane polymers, functionalised molecular silica compounds, such as Vinyl Q® and P.O.S.S. compounds. Very good results, in particular in combination with a silicon (pre-)polymer as a matrix pre-polymer, have been achieved with a polyalkylhydrosiloxane polymer. When used in combination with a silicon (pre-)polymer as a matrix pre-polymer, the molar ratio of hydride to vinyl functional groups is preferably 1:1 to 10:1.

A preferred polyalkylhydrosiloxane polymer as a curing agent is a copolymer of alkylhydrosiloxane moieties and dialkylsiloxane moieties, preferably of methylhydrosiloxane moieties and dimethylsiloxane moieties.

Preferably the amount of dialkylsiloxane moieties—in particular dimethylsiloxane moieties—and/or the amount of alkylhydrosiloxane moieties—in particular methylhydrosiloxane moieties—in a polyalkylhydrosiloxane polymer is 1-100, and more preferably 5 to 20. The dialkylsiloxane-alkylhydrosiloxane copolymer may be a random, alternating or block copolymer.

As a filler any physiologically acceptable filler can be used. The filler may for example by essentially spherical, filament-like, disc-like or an agglomerate of smaller nanofiller particles.

In practice, the number average particle diameter of the fillers is in the range of 10 to 50 000 nm, preferably in the range of 10-1000 nm, more preferably in the range of 10 to 500 nm Very good results have been achieved with a nano-particle filler which have a relatively high specific area (characterised by a high BET-value), typically in the range of 50 to 400 $m^2/g$., in particular with hybrid-nanofillers i.e. a filler that not only acts as a filler, but that also contains reactive sites, e.g. vinyl groups, that are capable of participating in the curing of the composition. A hybrid-nanofiller has not only been found to have a positive effect on the mechanical properties after curing, but is also found that these hybrid fillers do not lead to adverse physiological reactions, or at least are less prone to lead to adverse physiological reactions in comparison to several ordinary fillers.

It is also possible to use a combination of different fillers. It has for example been found that a combination of a hybrid-nanofiller, in particular a silica based hybrid-nanofiller, in combination with a hydrophobic filler, in particular a silica hydrophobic filler.

The amount of filler in the composition depends inter alia on the type of filler, its contribution to the viscosity of the composition. Also the desired characteristics of the composition after curing may play a role in determining the concentration. The skilled professional will readily be able to determine a suitable concentration. Typically the filler is present in an amount of at least 1 wt. %, based on the total weight. The upper limit is essentially determined by the amount of other constituents, present in the composition. For practical reasons, the amount of filler is usually less than 50 wt. %, based upon the total weight of the composition. Preferably the concentration is at least 2 wt. %, more preferably at least 15 wt. %. The amount of filler is preferably less than about 45 wt. %, more preferably less than about 40 wt. %. Very good results have been achieved with a filler concentration of 25 to 45 wt. %.

Examples of suitable fillers are fillers selected from the group consisting of silica, clay, mica, calcium carbonate, fibre glass, polyethylene-naphthalate and combinations thereof, which may be present in unmodified or chemically modified form. Preferred is a nano-sized silica filler, e.g. a molecular silica filler. It has been found that silica not only contributes particular well to mechanical properties, but also is suitable as a contrast agent, e.g. for X-ray monitoring.

Preferably, the surface of the filler is hydrophobic, e.g. due to chemical modification. The term hydrophobic filler is used herein to describe a filler, of which the surface has been treated with a non-polar compound that dissolves better (i.e. has a higher solubility) in an organic solvent such as an alkane than in water.

It has been found that such a filler contributes very satisfactorily to the mechanical properties of the composition after curing and also has only a relatively small effect on the flowability in comparison to hydrophilic fillers.

A preferred hydrophobic filler is a filler, more preferably a silica filler, wherein at least the surface has been modified with an organosilicon compound, e.g. with dichlorodimethylsilane ($(CH_3)_2SiCl_2$), hexamethyl-disilazane ($[(CH_3)_3Si]_2NH$) or reactive polydimethylsiloxanes. Such fillers are readily available in the market, e.g. Aerosil R8200 (Degussa), functionalised molecular silica (e.g. Vinyl Q® (Gelest, USA)). Besides the excellent mechanical properties of a cured material, obtained from a composition comprising a surface modified silica filler, it has been found that such a filler may also serve as a contrast agent as an alternative to commonly used separate contrast agents, or to be used in combination with (reduced concentration of) such a contrast agent.

Very good results have been realised with a filler modified with vinylalkylsiloxane, in particular a filler modified with vinyldimethylsiloxane. A cured material based upon a composition comprising vinylalkylsiloxane modified filler has been found to have particularly good mechanical properties and durability, after implementation in the body, in particular in combination with a silicon (pre-)polymer as a matrix pre-polymer and/or a alkylhydrosiloxane as a curing agent. Besides good mechanical properties for a prolonged period, it has been found that such a composition has a very advantageous light transparency and curing behaviour.

A composition according to the invention may essentially consist of matrix pre-polymer, curing agent and filler. A composition may comprise one or more additives, e.g. one or more additives selected from the group consisting of contrast agents, curing inhibitors and chain extenders.

As indicated above, in particular silica may be present not only as a filler but also as a contrasting agent. Other examples of particularly suitable contrast agents include iodine based contrast agents (containing iohexyl e.g. Omnipaque®, (supplied by Nycomed). An iodine based contrast agent (such as Omnipaque®) is a preferred contrast agent, in that it has been found that it does not adversely affect the curing process.

A chain extender may be present in a composition to change the elasticity modulus and/or the elongation until rupture of a cured material with. Suitable examples of chain extenders include hydride terminated polydimethyl siloxanes.

Very good results have been obtained with a chain extender, present in a composition according to the invention in a concentration of 1-10 wt. % based upon the combined weight of filler, matrix pre-polymer and curing agent.

Curing inhibitors may be present in the composition to improve stability of the composition until the curing is induced, shortly before application of the composition. An examples of a curing inhibitors is 1,3,5,7-tetravinyl-1,3,5,7-tetramethylcyclotetrasiloxane.

The curing may be initiated and propagated in any way suitable to cure the particular combination of matrix pre-polymer and curing agent as long as this curing is physiological acceptable. The curing may for example be started under influence of radiation, e.g. electromagnetic radiation or chemically, e.g. by an added catalyst or reactant or by a component that is naturally present in the body, e.g. water or particular ions.

Preferably the curing is performed under influence of a curing catalyst. The curing catalyst may for example be present in a composition comprising a matrix pre-polymer, a filler and/or other additives. In particular if such a curing catalyst composition comprises a matrix pre-polymer, it will usually be essentially free of curing agent.

It has been found that by using a curing catalyst, a cured material is obtained that has very favourable mechanical properties throughout the material.

Very good results have been achieved with a platinum catalyst, in particular for curing a composition comprising a matrix pre-polymer with vinyl units as reactive site and a curing agent with hydride units as active site.

Highly preferred examples of platinum catalysts are platinum complexes, in particular platinum complexes selected from the group consisting of platinum-divinyltetramethyldisiloxane complexes. Good results have inter alia been realised when using such a complex in a concentration of 2 to 7 ppm Pt based upon the total weight of the composition.

The concentration of curing catalyst can readily be determined depending upon the composition and the desired curing time. For example for curing a composition comprising a silicon (pre-)polymer, in particular a polydialkylsiloxane polymer comprising at least two vinyl groups, and a polyalkylhydrosiloxane polymer, good results have been achieved with a platinum catalyst in a concentration of at least 5 ppm (based upon the total weight of the biocompatible polymer composition). Particular favourable with respect to the curing time has been found to be a concentration of about 5 to 500 ppm.

The curing catalyst is preferably mixed with the composition, shortly before applying the composition to the body vessel or cavity. Very good results have been achieved by mixing a composition comprising a curing catalyst with a biocompatible polymer composition according to the invention in a static mixer, in particular in a static mixer comprising at least 30 mixing elements. Static mixers are readily available in the market. They comprise an elongated channel wherein for example a multi-helical screw is placed along which the fluids are passed and mixed. Herein each winding of the screw is considered as a single mixing element.

The present invention further relates to the use of a biocompatible polymer composition according to the invention or a curing catalyst composition to the invention, in the manufacture of a pharmaceutically acceptable composition for the treatment, in particular the in vivo repair, of an aneurysm and to the use of such composition in the manufacture of a physiologically acceptable composition for securing a stent or stent-graft in an artery.

The present invention further relates to a kit of parts for use in an in vivo aneurysm repair, comprising a biocompatible polymer composition according to the invention, and a curing-catalyst composition.

Preferably the curing catalyst composition in a kit according to the invention comprises at least one component selected from the group consisting of matrix pre-polymers, fillers and contrast agents.

Very good results have been realised with a kit, wherein the viscosity of the curing catalyst composition is at most 1 500 cSt higher or lower than the viscosity of the biocompatible polymer composition.

A particularly preferred kit comprises a biocompatible polymer composition and a curing-catalyst composition in amounts in viscosities such that the mixture of biocompatible polymer composition and a curing-catalyst composition has a viscosity of 2 000-12 000 cSt at 25° C.

Much preferred is a kit, wherein the biocompatible polymer composition mixed with the curing catalyst composition, has a curing time of 5 min or less, more preferably 2 to 3 min.

For typical applications the amount of biocompatible polymer composition and curing agent composition is such that their total weight when mixed is 20 to 500 grams.

As indicated above, a composition according to the invention is suitable for treating a body cavity or vessel. A composition according to the invention is in particular suitable for forming a stent in situ inside a body vessel, more in particular for repairing an aneurysm in an artery, e.g. the aorta. The polymer composition can be introduced at the site that is to be treated by any delivering system suitable for delivering fluid compositions in a body. Examples of such delivering systems and methods of applying the composition are readily known in the art, e.g. from the publications mentioned herein, e.g. Dutch patent 1 005 190.

Accordingly, the present invention also relates to a method of treating a body cavity or body vessel—preferably an aneurysm in a blood-vessel, with a composition according to the present invention, said method comprising the steps of covering the inner wall of the vessel or cavity with an essentially cylindrical layer of the composition and curing the composition. Obviously the curing by and large takes place after covering the inner wall, although it is possible that the curing is initiated shortly (typically up to about 1-10 min) before applying the composition to the wall.

In an embodiment, the composition is applied to the inner wall by using an apparatus comprising a catheter with at the distal end an expandable, essentially cylindrical carrier, which carrier is inserted in the vessel or cavity, wherein the composition is applied between the outer wall of the carrier and the inner wall of the vessel or cavity, wherein the carrier is expanded and has—in expanded state—at least one, preferably two rounded shoulders, at a distance from one another, which shoulders are in contact with the cavity or vessel wall, such that a filling space for the composition is formed between the two shoulders, the outer wall of the carrier and the inner wall of the vessel or cavity, and wherein this filling space is provided with the composition. The composition can for example be applied to the filling space via one or more holes in the carrier.

A preferred example of a carrier is a balloon that is expansible under influence of pressure, e.g. transferred via a liquid or a gas. The balloon is brought to the site to be treated, e.g. the aneurysm, where it is expanded. Via a catheter, the composition is then injected into the space between balloon and vessel wall. FIG. 1 shows an example of an aneurysm in the aorta. The arteries 1 are temporarily blocked from blood circulation with the help of three balloon catheters 2. As shown in this figure each of the balloons has one rounded shoulder 2a. One catheter comprises an echo sounder 4 to locate the renal arteries 1a and 1b. The biocompatible polymer composition—mixed with a curing catalyst composition is injected via another catheter or a needle that has also been introduced at the aneurysm via an artery.

The invention further relates to the treatment of a bone with a curable polymer composition.

It has been found that a human or an invertebrate in general may be effectively treated with a curable polymer composition in order to reduce the risk of complications of a future bone fracture.

The bone treated in accordance with this aspect of the invention is preferably a collarbone or a hip.

Typically the (non-broken) bone is provided with a curable polymer composition. Suitable compositions are known in the art, e.g. as described herein or in one of the references cited in the present description.

Preferably the curable polymer composition is a composition as described in the present claims and/or description, although other composition may suitably be employed.

Figure 4:
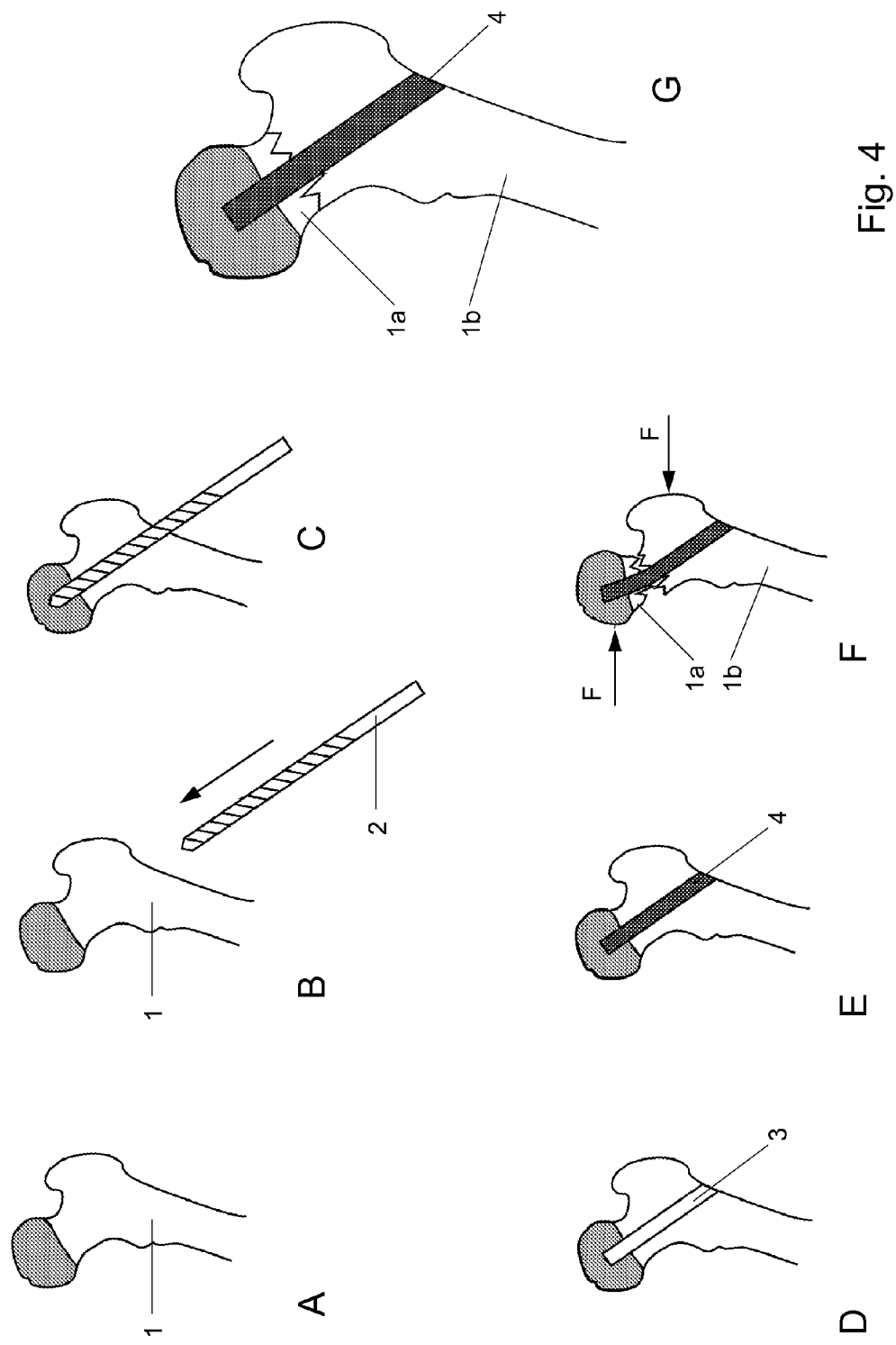
FIGS. 4A-4G schematically depict how a bone may be provided with the curable composition described herein.

In accordance with a method for treating a bone, a cavity is made in the bone, which may be done by a method generally known in the art, e.g. in a way known to introduce osteosynthetic material into a bone. Thereafter the cavity is provided with the curable composition and the composition is cured. FIG. 4 schematically shows by means of an example how a bone may be provided with the curable composition. FIG. 4A shows how a drill 2 is directed at a bone 1 and used to drill a hole (FIGS. 4B and 4C). Removal of the drill 2 provides a cavity 3 in the bone (FIG. 4D) that is filled with the curable composition 5 (FIG. 4E), which is subsequently allowed to cure. If—at a later moment—the bone is fractured (FIG. 4F; arrows F indicate where forces are applied), the cured composition keeps the fractured bone parts 1a and 1b in place, or at least reduces shifting of the bone parts (FIG. 4G).

The cavity is preferably provided along at least a substantial part of the bone, for instance by drilling, and filled with the curable composition, after which the composition is cured. The cured composition thus preferably forms an elastic rod-like structure.

If the bone breaks after the composition is cured, the cured composition maintains or swiftly brings back the broken parts essentially in the right position, thus avoiding or at least reducing the risk of complications due to shifting of the bone parts.

Such a method may for instance very suitably be carried out in combination with a surgery that has to be performed on a patient for an acute reason, for instance on a patient of which one of the hips or one of the collarbones has been broken.

Accordingly, the invention also relates to the use of a curable polymer compositions in the manufacture of a physiologically acceptable composition for prophylactic treatment of a bone, preferably a hip or a collarbone. Such prophylactic treatment helps to avoid or at least reduces the risk of complications after fracture.

The invention is further illustrated by the following examples

Example 1

Polydimethyldiloxane (PDMS) vinyl terminated oligomers (supplied by Gelest, USA) were mixed with various weight percent of filler (Vinyl Q®) (supplied by Gelest, USA) in the range 0 to 50% w/w and with different hydride methyl siloxane (hydride HMS-301™, supplied by ABCR, Germany. concentrations as well as different platinum concentrations, The platinum compound was platinum-divinyltetramethyldisiloxane complex, 3-3.5% platinum concentration in vinylterminated ploydimethylsiloxane, supplied by ABCR, Germany.

The formulations providing the best viscosity and mechanical properties following the protocol are obtained at a weight percent above 25% of vinyl Q® in 1000 cSt PDMS vinyl terminated. The viscosity of the formulation containing 20% w/w Vinyl Q® in 1000 cSt PDMS vinyl terminated oligomer was found to be 4 000 cSt.

The addition of 5% Aerosil R8200™ (supplied by Degussa, Germany) to the 20% w/w Vinyl Q®, was found to accelerate the cure rate, increase the mechanical properties. The viscosity increase varied from no significantly increase in the start viscosity up to an acceptable increase from 4 000 to 5 000 cSt.

The 50% w/w Vinyl Q® in 1 000 cSt PDMS vinyl terminated provided a viscosity of 7 000 cSt.

Example 2

The following basic formulation was made:
20% w/w vinyl Q® (molecular filler)
70% w/w 1000 cSt PDMS vinyl terminated
10% w/w silica Aerosil R8200™

The composition was prepared as follows: The vinyl Q® was added to the PDMS. After gently mixing until a homogenous mixture was formed the silica Aerosil R8200™ was added in small quantities at a time to 200 g of PDMS/Vinyl Q®, and was vigorously mixed with a Kinematica high shear mixer (Kinematica PT-MR 3000 EU/502) for one hour at 25 000 rpm. The resulting mixture was homogenous.

From the resulting basic formulation of PDMS/vinyl Q®/silica two components (A and B) were prepared. Component A contained 6 g hydride having 10 functional (HMS-301) in 24 g of PDMS/vinyl Q®/silica, and component B contained 2.4 g platinum from a 0.0286% complex platinum (as in Example 1) added to 26 g PDMS/vinyl Q®/silica. The material was cured at to form sheets of 10 cm×10 cm×2 mm. It was found that the chain extender influenced the cured material, by reducing the tensile modulus and increasing the maximum elongation.

In a tensile strain test, a sample of the cured material was strained at 60% from its original length and subjected to 100% stretch at 1260 cycles per minute. The sample was tested for a life time equivalent to at least 10 years of stretching in vivo (heart rate 60 BPM). The properties still were satisfactory at the end of the test.

Example 3

The following basic formulation was made as indicated in Example 2
30% Vinyl Q® w/w
67% 1000 cSt PDMS vinyl terminated
3% w/w silica Aerosil R8200™

The component A contained 7 g HMS-301™ (9% of the total formulation weight), plus 23 g of the basic 30% w/w Vinyl Q® formulation given above, while component B contained 3 g platinum at 0.0286% complex platinum in PDMS 1000 cSt plus 27 g from the basic formulation (with 30% Vinyl Q®).

A cylindrical test sample was produced by mixing component A & B and curing the composition. Curing was performed at room temperature to produce sheets as indicated in Example 2. In addition, a cylindrical aneurysm-type of shape was produced to fit the material to be tested in long term experiments. The cylindrical test sample was connected to an air pressure at 0.5 bar, inflating each 0.3 seconds for two months before stopping the experiment. The sample did not show any signs of fatigue or deterioration.

Example 4

Four samples (with a total weight of 60 grams) were produced based on 1000 cSt PDMS vinyl terminated, each having the same filler concentration of 35.5 wt. % of Vinyl Q®, 5 wt. % silica from Aerosil R8200™, each having the same platinum concentration 0.2 g at 3 wt. % complex platinum in PDMS 1 000 cSt., but having different hydride concentration (HMS-301™).

The HMS-301™ quantities per 60 g sample were as follows:

Example 4.1: 6.0 gr. HMS-301™
Example 4.2: 6.5 gr. HMS-301™
Example 4.3: 7.0 gr. HMS-301™
Example 4.5: 7.5 gr. HMS-301™

Cured samples (as indicated in Example 3) were connected to an air pressure of 0.5 bar, inflating each 0.3 seconds. After 4 months of testing, the sample did not show any signs of fatigue or deterioration.

Example 4.2 showed the best results with respect to Young' modulus, elongation and tear resistance.

Example 5

The following basic formulation was made
49 wt. % Vinyl Q®
1.1 wt. % silica from Aerosil R8200™
49.9 wt % 1000 cSt PDMS vinyl terminated As component A, a mixture was made containing 11 g HMS and 19 g from the 49% w/w vinyl Q® basic formulation, and component B containing 0.4 gr platinum at 3% complex platinum in PDMS 1000 cSt and 29.6 gr from the same basic Vinyl Q® formulation.

It was found that a cured test sample produced with this composition was more rigid than any of the samples made in Examples 1-4 or a test sample made with clay or mica as nanofiller.

A cylindrical test sample was connected to an air pressure of 0.5 bar, inflating each 0.3 seconds. After 4 months of testing, the sample did not show any signs of fatigue or deterioration.

Example 6

Figure 2:
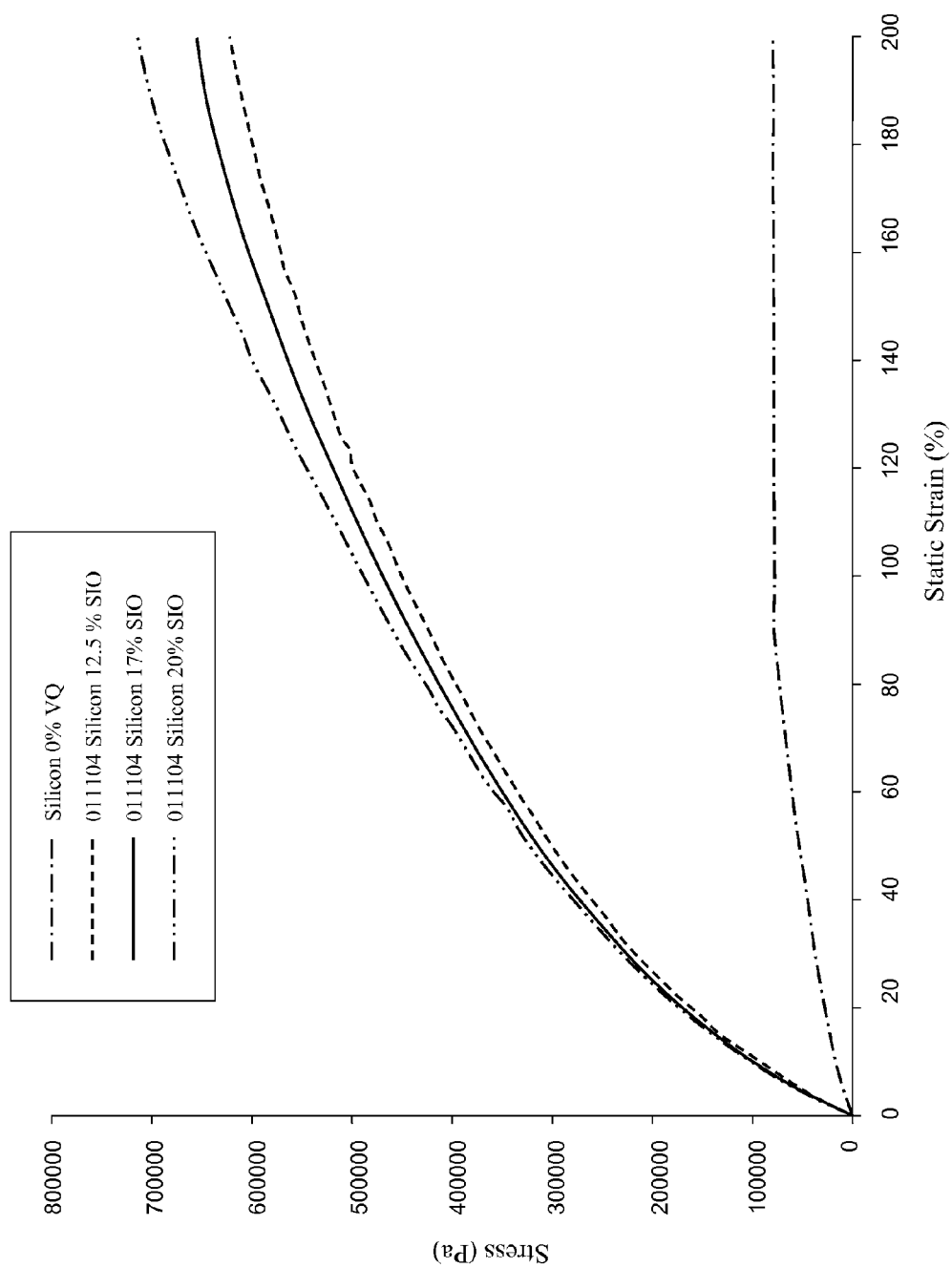
FIG. 2 graphically depicts the effect of the percent of added silica filler on the overall mechanical properties such as stress and strain.

The modulus of cured silicone compositions, to be used as aorta implant were measured using the Dynamic Mechanical Analyser (DMA 7 from Perkin Elmer), in the stress-strain mode. The strength until sample rupture was determined from samples which were hold between air-pressurised grips within the Zwick 1445. The mechanical properties were observed to be reproducible within an error of 5%. The effect of the percent of added silica filler on the overall mechanical properties such as stress and strain are shown in FIG. 2. The elastic modulus of a cured composition is determined by the initial slope of the corresponding curve.

There was a huge stress difference between a silicone system containing 0% silica and that containing 12.5%. The static strain was not significantly different between the different samples until 200% stretching.

Also, no appreciable difference in stress existed in between silicone systems having 12.5% and those having 20% silica.

The silicone/silica systems having 20% silica showed the highest tear strength.

Example 7

The stress strain curve of the following systems was determined: silicone 0% silica, silicone with 20% vinyl Q® and 7% silica, silicone with 30% Vinyl Q®, silicone with 34% vinylQ®, silicone 34% Vinyl Q® and 4% silica with 1% microfibres, silicone with 34% vinyl Q® and 4% silica, and silicone with 35% vinyl Q® and 5% silica. Otherwise the conditions were as indicated in the previous Examples.

Figure 3:
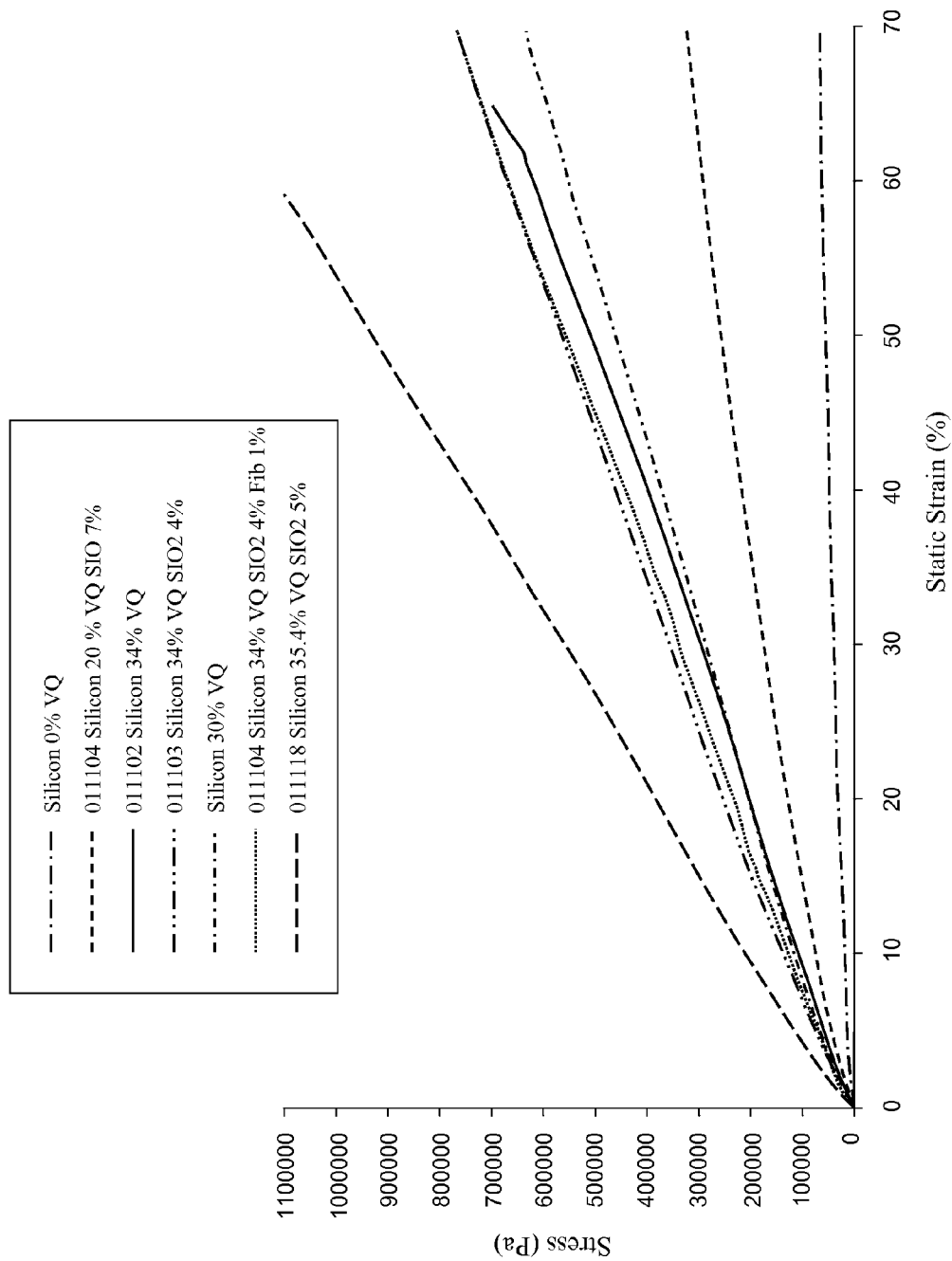
FIG. 3 graphically depicts a stress strain curve of silicone 0% silica, silicone with 20% vinyl Q® and 7% silica, silicone with 30% Vinyl Q®, silicone with 34% vinylQ®, silicone 34% Vinyl Q® and 4% silica with 1% microfibres, silicone with 34% vinyl Q® and 4% silica, and silicone with 35% vinyl Q® and 5% silica.

The results are shown in FIG. 3.

Example 8

The Vinyl Q®/PDMS/silica nanofiller formulations of examples 1-7 were put in glass pots and were brought to 200° C. for 15 minutes. No effect of temperature on the pre-polymerisation and/or crosslinks was noticed, which demonstrates that a silicon (pre-)polymer based composition according to the invention can easily be sterilized.

The invention claimed is:

1. A method for treating a bone comprising the steps of:
   making a cavity in the bone;
   providing the cavity with a curable polymer composition; and
   curing the composition to form a cured composition, wherein the cured composition has an elongation until rupture of at least 10%.

2. The method according to claim 1, wherein the cured composition has an elongation until rupture of at least 25%.

3. The method according to claim 2, wherein the cured composition has an elongation until rupture of at least 50%.

4. The method according to claim 1, wherein the cured composition has an elastic modulus of at least 2 MPa.

5. The method according to claim 1, wherein the curable polymer composition includes a curing agent.

6. The method according to claim 1, wherein the step of curing the composition is initiated and propagated by radiation.

7. The method according to claim 1, wherein the curable polymer composition includes a curing catalyst.

8. The method according to claim 7, wherein the curing catalyst is a platinum catalyst.

9. The method according to claim 1, comprising the step of mixing a curing catalyst with the curable polymer composition in a static mixer, and thereafter providing the cavity with the mixture.

10. The method according to claim 1, wherein the bone is a hip or a collar bone.

11. The method according to claim 1, wherein the curable polymer composition comprises a matrix pre-polymer, a curing agent and an additive.

12. The method according to claim 11, wherein the additive is one or more members selected from the group consisting of fillers, contrast agents, curing inhibitors and chain extenders.

13. The method according to claim 1, wherein the cured composition forms an elastic rod-like structure.

14. The method according to claim 1, wherein the curable polymer composition is biocompatible and includes a matrix pre-polymer, a filler and a curing agent, wherein said biocompatible polymer composition is curable in the presence of a curing catalyst at 37° C. to form the cured composition having an elongation until rupture of at least 10% and an elastic modulus of at least 1 MPa.

15. The method according to claim 1, wherein the curable polymer composition includes a silicon (pre-)polymer.

* * * * *